United States Patent
Schick

(10) Patent No.: US 6,206,892 B1
(45) Date of Patent: Mar. 27, 2001

(54) INSTRUMENT FOR REMOVING TICKS

(75) Inventor: Gerhard Schick, Sinsheim (DE)

(73) Assignee: Fortuna Vertrieb Dr. G. Schick GmbH, Sinsheim (DE)

( * ) Notice: Subject to any disclaimer, the term of this patent is extended or adjusted under 35 U.S.C. 154(b) by 0 days.

(21) Appl. No.: 09/384,702

(22) Filed: Aug. 27, 1999

(30) Foreign Application Priority Data

Aug. 27, 1998 (DE) ............................................... 198 38 961

(51) Int. Cl.[7] ................................................... A61B 17/50
(52) U.S. Cl. .............................................. 606/131; 606/210
(58) Field of Search .................................... 606/131, 205, 606/210, 211; 119/626; 294/3, 99.2

(56) References Cited

U.S. PATENT DOCUMENTS

| | | | |
|---|---|---|---|
| 277,531 | * | 5/1883 | Ackermann . |
| 4,303,268 | * | 12/1981 | Davidson .......................... 606/210 X |
| 4,976,718 | | 12/1990 | Daniell . |
| 5,002,323 | * | 3/1991 | Idsund .............................. 606/210 X |
| 5,116,347 | | 5/1992 | Butler . |
| 5,431,665 | * | 7/1995 | Li ........................................ 606/131 |
| 5,447,511 | | 9/1995 | Gadd . |
| 5,554,161 | | 9/1996 | Thibeault . |
| 5,595,569 | | 1/1997 | Hebbard . |
| 5,607,434 | | 3/1997 | Alvino . |
| 5,843,094 | * | 12/1998 | Saylor ................................. 606/131 |
| 5,876,409 | * | 3/1999 | Heitz .................................. 606/131 |
| 5,998,762 | * | 12/1999 | Von Der Heyde ................... 219/229 |

FOREIGN PATENT DOCUMENTS

| | | |
|---|---|---|
| 8319104 | 12/1983 | (DE) . |
| 29617656 U1 | 1/1997 | (DE) . |
| 19652218 A1 | 6/1998 | (DE) . |
| 0717963 A1 | 6/1996 | (EP) . |

* cited by examiner

Primary Examiner—Jeffrey A. Smith
(74) Attorney, Agent, or Firm—Alston & Bird LLP

(57) ABSTRACT

An instrument for removing ticks from the skin of a person or animal and which includes a handle portion and a pickup device on one end of the handle portion. The pickup device includes a circular base wall having a V-shaped slot, and cylindrical jacket joined to the base wall. The cylindrical jacket includes a radial passage which is aligned with the open end of the slot. In use, the base wall is placed on the skin and the base wall is then slid along the skin to cause the tick to be received in and engaged by the slot, with the body of the tick entering the cylindrical jacket.

16 Claims, 4 Drawing Sheets

INSTRUMENT FOR REMOVING TICKS

BACKGROUND OF THE INVENTION

The present invention relates to an instrument for removing ticks with a gripping handle portion which is similar to pliers.

Instruments for removing ticks have been known for a long time, and they exist in a large variety of shapes and sizes. Frequently, the instruments are constructed in the form of tweezers. Such instruments are used both in the private and the commercial fields, when ticks are to be removed from the human or animal skin, to which they are attached. Such a removal of ticks from the skin is necessary, since a bite of the ticks may transmit dangerous diseases to the human and domestic animals. Both during the removal by means of fingers and by means of tweezers, it is possible to tear off in most cases only the body of the tick that swells considerably during the sucking of blood, whereas the mouthparts of the tick continue to be attached in the skin. In this state, it is still possible to transmit diseases.

A complete removal of a tick while it sucks blood, can be realized in most cases only with a good feel for gripping or holding and by subsequently twisting out the mouthparts of the tick. In this connection, the twisting motion effects a cautious pulling of the tick. Further, the twisting motion accomplishes a stabilization between the mouthparts and the tick body, so that the known instrument is capable of preventing in nearly all cases a tearing of the mouthparts.

However, the known instruments are problematic, in that despite gripping the tick with a special gripping arrangement, it is not always possible to avoid having the fully bloated body of the tick be squashed and exploded. The risk of squashing and exploding the tick body exists in particular in a strongly bloated state of the tick body. Thereafter, a safe and clean removal of the tick is no longer ensured.

It is therefore the object of the present invention to provide an instrument of the initially described kind for removing ticks, which facilitates an easy removal of ticks from the skin with a simplest handling, even when the body of the tick is strongly bloated.

SUMMARY OF THE INVENTION

The above and other objects and advantages of the invention are achieved by the provision of an instrument which comprises a handle portion and pickup device mounted to one end of the handle portion. The pickup device comprises a base wall which has a slot therein for receiving a tick which is attached to the skin of a person or animal, as the base wall of the instrument is slid over the surface of the skin.

The pickup device and, more specifically, the slot make it possible to pick up and twist out or extract a tick in a simple manner, without incurring the risk of squashing the tick body by a gripping motion or a gripping in the fashion of pliers having gripping elements moving toward each other. In so doing, it is possible to pick up the tick simply between its mouthparts and body.

The construction of the instrument with both a gripping handle portion and a pickup device produces an instrument that always offers a suitable removing instrument in a combined manner both for not yet strongly bloated or not even bloated tick bodies and for very highly bloated tick bodies.

Consequently, the instrument for removing ticks in accordance with the invention, defines an instrument that facilitates with a simplest handling an easy removal of ticks from the skin, even in the case of highly bloated tick bodies.

With respect to a particularly simple pickup of a tick, it is possible to form the slot in a flat base wall of the pickup device. For picking up the tick, the instrument can be placed with its flat base wall on a correspondingly flat skin portion, and the pickup device can then be displaced on the skin portion such that the tick being removed is received in the slot. Thereafter, it is possible to twist or pull out the tick.

To ensure a particularly reliable pickup of the tick in the region of its mouthparts or between its mouthparts and body, the flat base wall can be made convex or substantially curved at least in the region of the slot. This ensures a safe sliding of the region of the slot directly on the skin. In other words, the flat base wall—proceeding from the region of the slot—curves away from the skin, on which the pickup device is placed.

As regards a particularly simple and reliable extraction of the tick, the flat base wall could have an inclination in the region opposite to the slot.

With respect to a reliable pickup of the tick, the slot can comprise two converging side walls. The tick would then be picked up preferably in the narrowest portion of the slot. In this connection, it will be advantageous, when the side walls converge at an acute angle, so that while picking up the tick, an engagement between the pickup device and the tick occurs as quickly as possible.

In a constructionally particularly simple configuration, it is possible to make the slot substantially triangular. In this connection, straight-line walls would be realized that are particularly simple to make.

With respect to a particularly reliable pickup of the tick, the walls can be inclined or sloped such that they form acute-angled pickup edges substantially opposite to each other. In this connection, a slope could be provided toward the plane of the flat base wall of the pickup device.

To prevent an unwanted tilting or even detaching of the tick body while it is being picked up, it is possible to slope the walls at the closed end of the slot such that they merge into one another continuously. Furthermore, it is possible to slope the walls along their entire length, including the closed end at the same angle. This angle may be about 45°, thus enabling a reliable removal of a tick.

In a constructionally simple and visually appealing configuration, the flat base wall can be formed as a base surface of a substantially cylindrical pickup device, which includes the slot. To ensure that the pickup range is as great as possible and thus reliable, the slot could extend from the periphery of the base wall to a point beyond the center of the circle defined by the base wall. In this connection, the slot could be formed as a slender gap.

The cylindrical pickup device can be formed by a cylindrical jacket which is joined at the periphery of the circular base wall. Furthermore, with respect to a reliable pickup of the tick or the tick body, the cylindrical jacket can include a radial passage in the region of the open end of the slot. It would then be possible to move the pickup device toward the tick in such a manner that the tick is moved through the open end of the slot and into the jacket. In so doing, the tick enters simultaneously through the radial passage of the cylindrical jacket into the interior of the jacket. Thus, the tick is partially surrounded by the cylindrical jacket.

To ensure a reliable pickup of even very large, i.e., very highly bloated ticks, the radial passage in the jacket can be formed approximately along the arc of half a circle of the circular base wall. This configuration would provide substantially the maximal passage with respect to a predetermined cylinder size.

In a constructionally simple manner, the pickup device can be attached to the end of the gripping handle portion facing away from the gripping member thereof. This would realize an instrument that comprises at its one end a gripping member and at its other end a pickup device.

In a further, constructionally simple manner, the pickup device can connect directly to the gripping handle portion. In this connection, an integral configuration with the gripping handle portion is advantageous. Also, the pickup device can either be cast with the gripping handle portion or be injection molded together with the gripping handle portion. It would be possible to use as material any plastic that is satisfactory to process.

To ensure a simple operation of the instrument, the gripping handle portion and/or the pickup device could be surrounded at least in part by a sleeve. Such a sleeve could be made of plastic or, in a particularly stable construction, of metal.

When the handle portion includes a sleeve, the gripping member can be arranged at one end of the sleeve and the pickup device at the other end thereof. In a particularly practical construction of the instrument, it would be possible to actuate the gripping member by pressing the pickup device. In this connection, it would again be of advantage to construct the instrument with a sleeve, since the actuation of the gripping member by pressing it with the thumb could occur while simultaneously holding the instrument in one hand. In this connection, the gripping arrangement could alternate with the sleeve for actuating its gripping elements.

BRIEF DESCRIPTION OF THE DRAWINGS

There exist various possibilities of developing and improving the teaching of the present invention in an advantageous manner. To this end, reference is made to the following description of an embodiment of the invention with reference to the drawings, in which.

DETAILED DESCRIPTION OF THE PREFERRED EMBODIMENT

Figure 1:
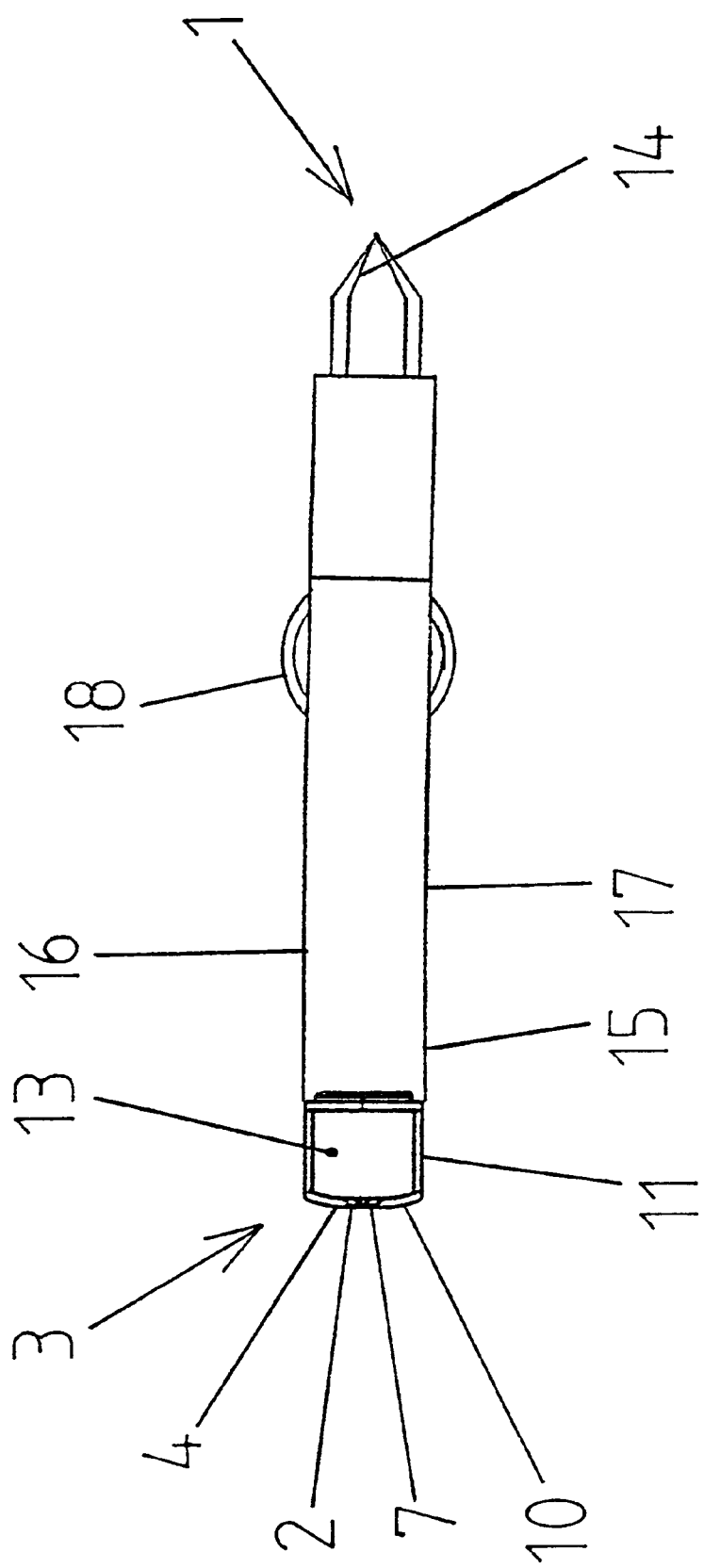
FIG. 1 is a schematic side view of an embodiment of the instrument according to the invention.

FIG. 1 is a schematic side view of an embodiment of an instrument for removing ticks in accordance with the invention. The instrument comprises a gripping handle portion 1 which comprises a pair of elongate arms similar to pliers. At one end of the handle portion, a pickup device 3 is mounted, which has a slot 2 for receiving a tick. The pickup device 3 facilitates an easy removal of ticks from the skin, even in the case of a highly bloated body, without incurring the risk of squashing or exploding the tick body.

To operate the instrument, a handle 16 surrounds the gripping handle portion 1 in part. The handle 16 is made as a sleeve 17 that facilitates turning the tick body, which is advantageous for removing the tick.

In the illustrated embodiment, the handle portion comprises a pair of elongate arms 19 which are joined to each other at a location adjacent the pickup device. The handle portion 1 is actuatable by means of actuation elements 18. In the alternative or in addition, the gripping handle portion 1 could be actuated by pressing the pickup device 3. In so doing, the gripping handle portion 1 would be displaced in sleeve 17.

More specifically, the pickup device 3 is arranged at the end 15 of the gripping handle portion 1, which faces away from the gripping member 14 of the gripping handle portion 1. The pickup device may be made integral with the gripping handle portion 1.

The slot 2 is formed in a generally flat base wall 4 of pickup device 3, and comprises two converging side walls 7. The slot 2 thus defines an open end 12 and a closed end 9.

The base wall 4 is generally circular in outline, and the pickup device 3 further includes a cylindrical jacket 11 which is joined to the periphery of the base wall. The jacket 11 comprises in the region of the open end 12 of the slot 2, a radial passage 13 for receiving a tick body into the jacket.

Figure 2:
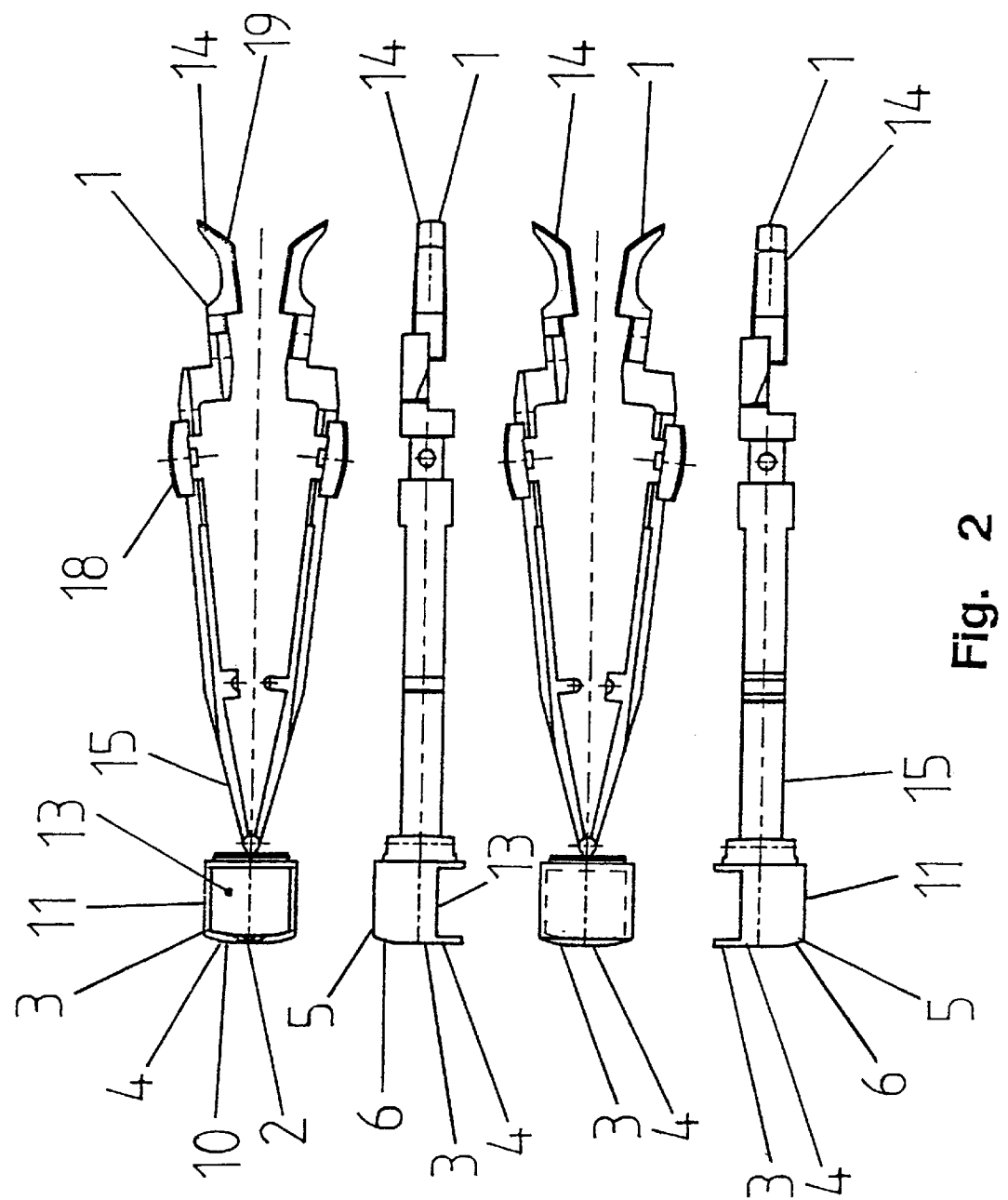
FIG. 2 shows four side views, each rotated by 90°, of the embodiment of an instrument according to the invention.

FIG. 2 illustrates four side views, each rotated by 90°, of the embodiment of an instrument according to the invention for removing ticks. The rotation occurs along the longitudinal axis of the gripping handle portion 1. For reasons of a better overview, the sleeve 17 is omitted. The pickup device is made integral with the gripping handle portion 1.

In the uppermost illustration of FIG. 2, the slot 2 opens toward the viewer. Both in the second and in the fourth illustration from the top, one can note that the flat base wall 4 exhibits a slope 6 in the region 5 opposite to the slot 2. This slope 6 is especially advantageous, when the tick is extracted, since the pickup device 3 and the flat base wall 4 will be able to slide easily over the skin of the human or animal.

In FIG. 2, the cylindrical shape of the pickup device 3 with a base surface 10 and a cylindrical jacket 11 is especially well seen. Furthermore, one can note in detail the construction of the gripping handle portion 1 with actuating elements 18.

The second and fourth illustration from the top each only show the upper gripping arm 19 in the direction of view.

Figure 3:
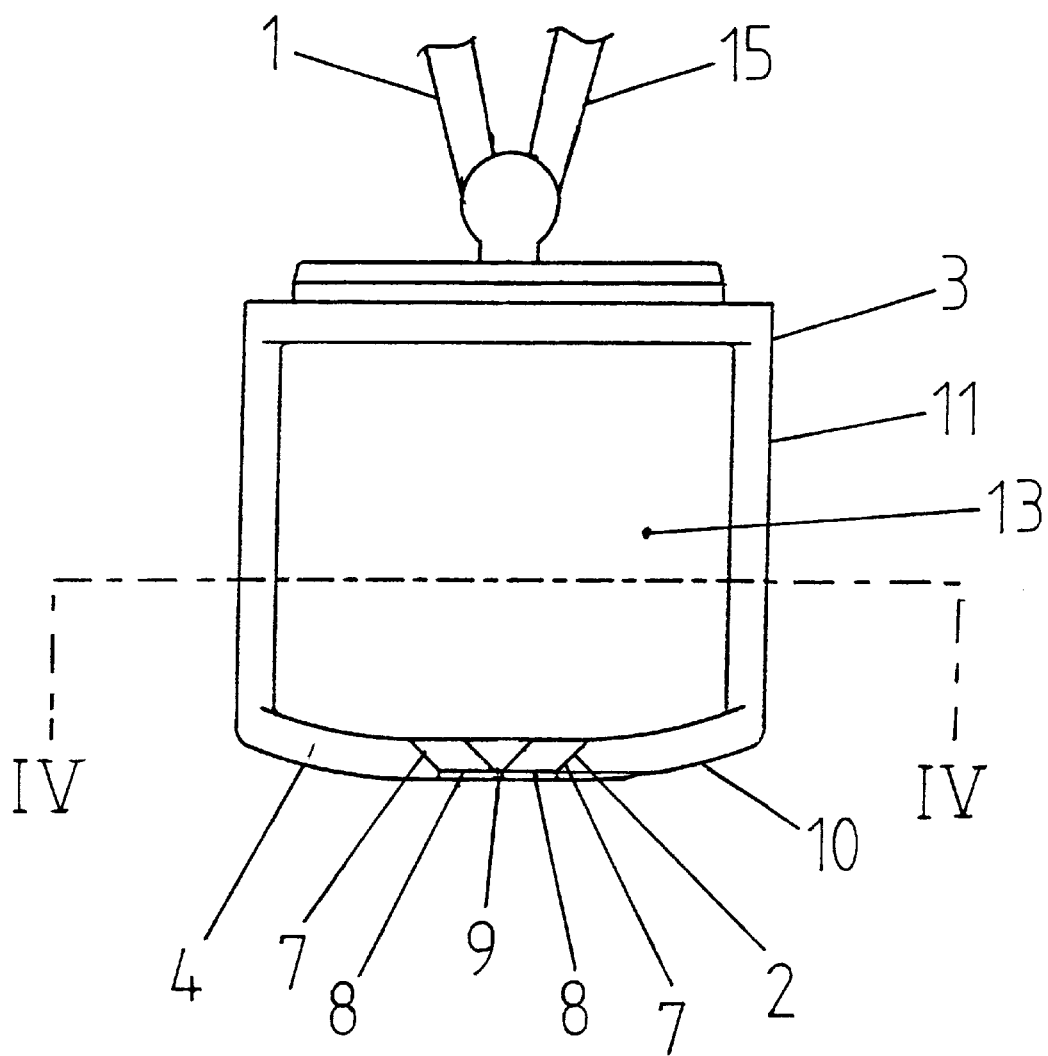
FIG. 3 is an enlarged side view of the pickup arrangement of the embodiment of FIG. 2.
Figure 4:
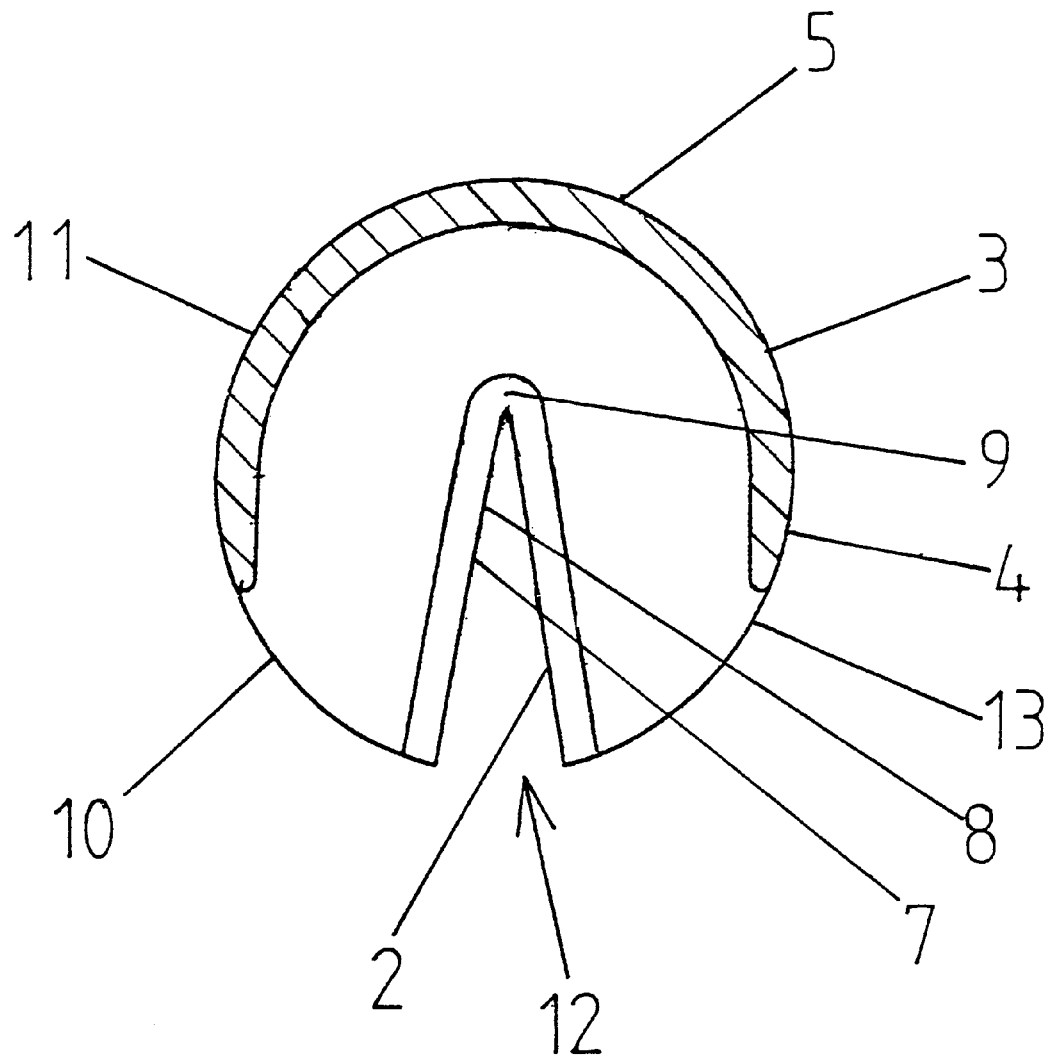
FIG. 4 is a sectional view of the embodiment of the pickup arrangement of FIG. 3 along line IV—IV.

FIGS. 3 and 4 are an enlarged side view as well as a sectional view along line IV—IV of FIG. 3 that shows the pickup device 3 of the embodiment of FIG. 2. The pickup device 3 comprises a substantially V-shaped or triangular slot 2. The slot 2 is formed in the flat base wall 4, which is made convex or substantially curved at least in the region of the slot 2.

The two converging walls 7 of the slot 2 are sloped such that they form substantially opposite, acute-angled pickup edges 8. The walls 7 are sloped in the closed end region 9 such that they merge into each other continuously. Furthermore, the walls 7 are sloped along their entire length, including closed end region 9, at the same angle of about 45°.

The slot 2 extends beyond the center of the circular periphery of base wall 4. The cylindrical jacket 11 includes a radial passage 13 in the region of the open end 12 of slot 2. In other words, the cylindrical jacket 11 does not extend along the entire periphery of the base wall 4. The radial passage 13 is formed approximately along the arc of about half of the periphery.

As regards further advantageous embodiments of the instrument for removing ticks, the background part of the specification as well the following claims are herewith incorporated by reference for purposes of avoiding repetition.

Finally, it should be emphasized that the above described embodiment of the instrument according to the invention serves only to explain the claimed teaching, however without limiting the scope to the specifically described embodiment.

What is claimed is:

1. An instrument for removing ticks comprising
   a handle portion,
   a pickup device mounted to one end of the handle portion, said pickup device comprising a base wall which has a slot therein for receiving a tick which is attached to the skin of a person or animal, and
   wherein said handle portion comprises a pair of elongate arms joined to the pickup device.

2. The instrument as defined in claim 1 wherein the base wall of the pickup device is curved at least in the region of the slot.

3. The instrument as defined in claim 1 wherein the slot is generally V-shaped and includes two converging side walls, and such that the slot defines an open end and a closed end.

4. The instrument as defined in claim 3 wherein the two side walls of the slot converge at an acute angle.

5. The instrument as defined in claim 4 wherein the two converging side walls are sloped at an acute angle when viewed in cross section.

6. The instrument as defined in claim 5 wherein the two converging side walls are sloped at the same angle along their entire length and so that they merge continuously at said closed end of the slot.

7. The instrument as defined in claim 3 wherein the base wall is generally circular, and wherein the pickup device further comprises a cylindrical jacket joined to the periphery of the generally circular base wall, with said jacket having a radial passage in the region of the open end of the slot, so that the body of a tick can extend through the slot and be received in the cylindrical jacket.

8. The instrument as defined in claim 7 wherein the radial passage extends along about one half the circular periphery of the base wall.

9. The instrument as defined in claim 3 wherein the base wall has a generally circular periphery, and wherein said slot extends from the periphery to a point beyond the center of the circular periphery of the base wall.

10. The instrument as defined in claim 3 wherein said base wall is generally flat and said elongate arms are joined to the pickup device so as to extend generally perpendicular to said base wall.

11. The instrument as defined in claim 1 wherein the pickup device is formed integrally with said handle portion.

12. The instrument as defined in claim 1 wherein said pair of elongate arms are joined to each other at a location adjacent the pickup device.

13. The instrument as defined in claim 12 further comprising a tubular sleeve substantially enclosing said handle portion in a surrounding relation.

14. An instrument for removing ticks comprising
   a handle portion,
   a pickup device mounted to one end of the handle portion, said pickup device comprising a base wall which has a slot therein for receiving a tick which is attached to the skin of a person or animal, and
   wherein the slot is generally V-shaped and includes two converging side walls, and such that the slot defines an open end and a closed end, and the base wall is generally circular, and the pickup device further comprises a cylindrical jacket joined to the periphery of the generally circular base wall, with said jacket having a radial passage in the region of the open end of the slot, so that the body of a tick can extend through the slot and be received in the cylindrical jacket.

15. The instrument as defined in claim 14 wherein said base wall is generally flat, and said pickup device further includes a top wall which is generally parallel to said base wall and is joined to an end of said cylindrical jacket which is opposite said base wall, and wherein said handle portion comprises a pair of elongate arms which are joined to said top wall so as to extend generally perpendicular thereto.

16. An instrument for removing ticks comprising
   a handle portion,
   a pickup device mounted to one end of the handle portion, said pickup device comprising a base wall which has a slot therein for receiving a tick which is attached to the skin of a person or animal, and
   wherein the slot is generally V-shaped and includes two converging side walls, and such that the slot defines an open end and a closed end, and the base wall has a generally circular periphery, and said slot extends from the periphery to a point beyond the center of the circular periphery of the base wall.

* * * * *